(12) United States Patent
Christakos et al.

(10) Patent No.: US 7,790,155 B2
(45) Date of Patent: Sep. 7, 2010

(54) CALBINDIN-D$_{28K}$ PROTECTION AGAINST GLUCOCORTICOID INDUCED CELL DEATH

(75) Inventors: Sylvia Christakos, Mendham, NJ (US); Yan Liu, Bloomfield, NJ (US); Teresita Bellido, Little Rock, AR (US)

(73) Assignee: University of Medicine and Dentistry of New Jersey, New Brunswick, NJ (US)

( * ) Notice: Subject to any disclaimer, the term of this patent is extended or adjusted under 35 U.S.C. 154(b) by 590 days.

(21) Appl. No.: 11/177,790

(22) Filed: Jul. 8, 2005

(65) Prior Publication Data

US 2005/0271627 A1  Dec. 8, 2005

Related U.S. Application Data

(63) Continuation-in-part of application No. 10/155,567, filed on May 23, 2002, now abandoned.

(51) Int. Cl.
 *A61K 48/00* (2006.01)
 *C12N 15/867* (2006.01)
 *C12N 15/861* (2006.01)
 *C12N 15/86* (2006.01)

(52) U.S. Cl. .................... 424/93.2; 435/456; 514/44

(58) Field of Classification Search .................. None
See application file for complete search history.

(56) References Cited

U.S. PATENT DOCUMENTS

| | | | |
|---|---|---|---|
| 5,139,941 A | 8/1992 | Muzyczka et al. | 435/172.3 |
| 5,288,641 A | 2/1994 | Roizman | 424/320.1 |
| 6,069,134 A | 5/2000 | Roth et al. | 514/44 |
| 6,319,495 B1 * | 11/2001 | Pollock et al. | 424/93.21 |
| 2003/0219421 A1 * | 11/2003 | Christakos | 424/93.21 |

OTHER PUBLICATIONS

Lomri et al., "Cloning and analysis of calbinden-D28K cDNA and its expression in hte central nervous system," Gene 80 (1): 87-98, 1989.*
Lomri et al., "Rat brain calbindin-d28k (CaBP28K) mRNA," GenBank Acc. No. M27839, US Natl. Library of Medicine, Bethesda, MD, USA, Apr. 27, 1993, accessed by PTO on Aug. 16, 2004.*
Bellido et al., "Calbindin-D28k is expressed in osteoblastic cells and suppresses their apoptosis by inhibiting caspase-3 activity," J. Biol. Chem. 275(34): 26328-26332,.2000.*
Ngo et al., "Computational complexity, protein structure prediction, and the Levinthal paradox," in The Protein Folding Problem and Tertiary Structure Prediction, Merz et al. (eds.), Birkhauser Boston: Boston, MA, pp. 433 and 492-495, 1994.*
Rudinger, J., "Characteristics of the amino acids as components of a peptide hormone sequence," (in Peptide Hormones, Parsons (ed.), University Park Press: Baltimore, MD, pp. 1-7, 1976.*
Orkin et al., Report and Recommentations of the Panel to Assess the NIH INvestment in Research on Gene Therapy, issued by the U.S. National Institutes of Health, Bethesda, MD, USA, Dec. 7, 1995.*
Verma et al., "Gene therapy—promises, problems and prospects," Nature 389: 239-242, Sep. 18, 1997.*
Rosenberg et al., "Gene therapist, heal thyself," Science 287: 1751, Mar. 10, 2000.*
Sequence Alignment—human and rat calbindin-D28k nucleic acids.*
Steinert et al. Biomaterials. Mar. 2008, 29(7): 904-916.*
Nixon et al. Ann. N.Y. Acad. Sci. 2007; 1117: 310-327.*
Verma et al. (Nature 389: 239-242, 1997).*
Orkin et al. (Report and Recommendations of the Panel to Assess the NIH Investment in Research on Gene Therapy. Dec. 7, 1995).*
Barr et al., "Apoptosis and Its Role in Human Disease", Bio/Technology 1994 12:487-493.
Bellido et al., "Calbindin-D$_{28k}$ Is Expressed in oSteoblastic Cells and Suppresses Their Apoptosis by Inhibiting Caspase-3 Activity", J. Biol. Chem. 2000 275(34):26328-26332.
Cheng et al., "IGF-I and IGF-II Protect Cultured Hippocampal and Septal Neurons against Calcium-mediated Hypoglycemic Damage", J. Neuroscience 1992 12(4):1558-1558.
Dowd et al., "Stable Expression of the Calbindin-D28K Complementary DNA Interferes with the Apoptotic Pathway in Lymphocytes", Molecular Endocrinology 1992 6:1843-1848.
Green, Douglas R., "Apoptotic Pathways:The Roads to Ruin", Cell 1998 94:695-698.
Guo et al., "Calbindin D28k blocks the proapoptotic actions of mutant presenilin 1:Reduced oxidative stress and preserved mitochondrial function", Proc. Natl. Acad. Sci. USA 1998 95:3227-3232.
Hughes et al., "Apoptosis in bone physiology and disease", J. Clin. Pathol. 1997 50:132-157.
Kalderon et al., "A Short Amino Acid Sequence Able to Specify Nuclear Location", Cell 1984 39:499-509.
Kitajima et al., "Induction of Apoptosis in Murine Clonal Osteoblasts Expressed by Human T-Cell Leukemia Virus Type I *tax* by NF-κB and TNF-α", Journal of Bone and Mineral Research 1996 11(2):200-210.
Liu et al., "Induction of Apoptotic Program in Cell-Free Extracts:Requirement for dATP and Cytochrome c", Cell 1996 86:147-157.
Manolagas S. C., "Editorial:Cell No. Versus Cell Vigor-What Really Matters to a Regenerating Skeleton?", Endocrinology 1999 140(10):4377-4381.

(Continued)

*Primary Examiner*—Scott Long
(74) *Attorney, Agent, or Firm*—Licata & Tyrrell P.C.

(57) ABSTRACT

The present invention provides novel compositions containing a calbindin-D$_{28k}$ therapeutic element, which is involved in the regulation of apoptosis, and may be administered for the prevention of an abnormal apoptosis response in cells. In particular the compositions and methods of the present invention may be used for the prevention or induction of apoptosis in such cells types as osteoblasts and osteocytes. Specifically, the compositions and methods of the present invention are useful for the prevention of diseases associated with glucocorticoid induced cell death. Specifically, the compositions and methods of the present invention may be useful in the prevention of glucocorticoid induced cell death in osteoblasts and the treatment of such conditions as glucocorticoid induced osteoporosis.

6 Claims, 1 Drawing Sheet

OTHER PUBLICATIONS

Mattson et al., "Fibroblast Growth Factor and Glutamate:Opposing Roles in the Generation and Degeneration of Hippocampal Neuroarchitecture", J. Neuroscience 1989 9(11):3728-3740.

Nieto-Bona et al., "Insulin-Like Growth Factor I Is an Afferent Trophic Signal That Modulates Calbindin-28kD in Adult Purkinje Cells", J. Neuroscience Research 1995 42:371-376.

Sonnenberg et al., "Vitamin D-Dependent Rat Renal Calcium-Binding Protein:Development of a Radioimmunoassay, Tissue Distribution, and Immunologic Identification", Endocrinology 1984 115(2):640-648.

Stashenko et al., "Effect of Immune Cytokines on Bone", Immunological Investigations 1989 18(1-4):239-249.

Steller, Hermann, "Mechanisms and Genes of Cellular Suicide", Science 1995 267:1445-1449.

Thornberry et al., "Caspases:Enemies Within", Science 1998 281:1312-1316.

Weinstein et al., "Inhibition of Osteoblastogenesis and Promotion of Apoptosis of Osteoblasts and Osteocytes by Glucocorticoids", J. Clinical Investigation 1998 102:274-282.

Wiley et al., "Identification and Characterization of a New Member of the TNF Family that Induces Apoptosis".

Wold, Finn, "Posttranslational Protein Modifications:Perspectives and Prospectives", Posttranlational Covalent Modifications of Proteins 1983 1-12.

Bellido et al., "Activation of the Janus Kinase/STAT (Signal Transducer and Activator of Transcription) Signal Transduction Pathway by Interleukin-6-Type Cytokines Promotes Osetoblast Differentiation", Endocrinology 1997 138 (9):3666-3676.

Bellido et al., "Transcriptional Activation of the p21 WAF1,CIP1,SDI1 Gene by Interleukin-6 Type Cytokines", J. Biol. Chem. 1998 172(22):21137-21144.

Centrella et al., "Tumor Necrosis Factor- Inhibits Collagen Synthesis and Alkaline Phosphatase Activity Independently of Its Effect on Deoxyribonucleic Acid Synthesis in Osteoblast-Enriched Bone Cell Cultures", Endocrinology 1988 123 (3):1442-1448.

Collazo et al., "Cellular Targets and Trophic Functions of Neurotrophin-3 in the Developing Rat Hippocampus", Neuron 1992 9:643-656.

Hill et al., "Multiple Extracellular Signals Promote Osteoblast Survival and Apoptosis", Endocrinology 1997 138 (9):3849-3858.

Jilka et al., "Osteoblast Programmed Cell Death (Apoptosis):Modulalion by Growth Factors and Cytokines", Journal of Bone and Mineral Research 1998 13(5):793-802.

Jilka et al., "Increased bone formation by prevention of osteoblast apoptosis with parathyroid hormone", J. Clinical Investigation 1999 104(4):439-446.

Kato et al., "Establishment of an Osteocyte-like Cell Line, MLO-Y4", Journal of Bone and Mineral Research 1997 12 (12):2014-2023.

Kluck et al., "The Release of Cytochrome c from Mitochondria:A Primary Site for Bg-2 Regulation of Apoptosis", Science 2997 275:1132-1136.

Miura et al., "Induction of Apoptosis in Fibroblasts by IL-1 -Converting Enzyme, a Mammalian Homolog of the C. elegans Cell Death Gene ced-3", Cell 1993 75:653-660.

Pansini et al., "Vitamin D-dependent Calcium-binding Protein in Rat Kidney", J. Biol. Chem. 1984 259(15):9735-9741.

Seifter et al., "Analysis for Protein Modifications and Nonprotein Cofactors", Methods in Enzymology 1990 182:626-646.

Wang et al., "Cleavage of sterol regulatory element binding proteins (SREBPs) by CPP32 during apoptosis", The EMBO Journal 1996 15(5):1012-1020.

Yang et al., "Prevention of Apoptosis by Bcl-2:Release of Cytochrome c from Mitochondria Blocked", Science 1997 275:1129-1132.

* cited by examiner

FIGURE 1

Effect of overexpression of calbindin-$D_{28K}$ on apoptosis MLO-Y4 cells

SEQUENCE LISTING

<160> NUMBER OF SEQ ID NOS: 4

<210> SEQ ID NO 1
<211> LENGTH: 786
<212> TYPE: DNA
<213> ORGANISM: Homo sapiens

<400> SEQUENCE: 1

```
atggcagaat cccacctgca gtcatccctc atcacagcct cacagttttt cgagatctgg       60
ctccatttcg acgctgacgg aagtggttac ctggaaggaa aggagctgca gaacttgatc      120
caggagctcc agcaggcgcg aaagaaggct ggattggagt tatcacctga aatgaaaact      180
tttgtggatc agtatgggca aagagatgat ggaaaaatag gaattgtaga gttggctcac      240
gtattaccca cagaagagaa tttcctgctg ctcttccgat gccagcagct gaagtcctgt      300
gaggaattca tgaagacatg gagaaaatat gatactgacc acagtggctt catagaaact      360
gaggagctta agaactttct aaaggacctg ctagaaaaag caaacaagac tgttgatgac      420
acaaaattag ccgagtatac agacctaatg ctgaaactat ttgattcaaa taatgatggg      480
aagctggaat taactgagat ggccaggtta ctaccagtgc aggagaattt tcttcttaaa      540
ttccagggaa tcaaaatgtg tgggaaagag ttcaataagg cttttgagct gtatgatcag      600
gacggcaatg gatacataga tgaaatgaa ctggatgctt tactgaagga tctgtgcgag       660
aagaataaac aggatctgga tattaataat attacaacat acaagaagaa cataatggct      720
ttgtcggatg gagggaagct gtaccgaacg gatcttgctc ttattctctg tgctggggat      780
aactag                                                                786
```

<210> SEQ ID NO 2
<211> LENGTH: 261
<212> TYPE: PRT
<213> ORGANISM: Homo sapiens

<400> SEQUENCE: 2

```
Met Ala Glu Ser His Leu Gln Ser Ser Leu Ile Thr Ala Ser Gln Phe
 1               5                  10                  15

Phe Glu Ile Trp Leu His Phe Asp Ala Asp Gly Ser Gly Tyr Leu Glu
                20                  25                  30
```

```
Gly Lys Glu Leu Gln Asn Leu Ile Gln Glu Leu Gln Gln Ala Arg Lys
        35                  40                  45

Lys Ala Gly Leu Glu Leu Ser Pro Glu Met Lys Thr Phe Val Asp Gln
 50                  55                  60

Tyr Gly Gln Arg Asp Asp Gly Lys Ile Gly Ile Val Glu Leu Ala His
 65                  70                  75                  80

Val Leu Pro Thr Glu Glu Asn Phe Leu Leu Leu Phe Arg Cys Gln Gln
                 85                  90                  95

Leu Lys Ser Cys Glu Glu Phe Met Lys Thr Trp Arg Lys Tyr Asp Thr
                100                 105                 110

Asp His Ser Gly Phe Ile Glu Thr Glu Glu Leu Lys Asn Phe Leu Lys
                115                 120                 125

Asp Leu Leu Glu Lys Ala Asn Lys Thr Val Asp Asp Thr Lys Leu Ala
            130                 135                 140

Glu Tyr Thr Asp Leu Met Leu Lys Leu Phe Asp Ser Asn Asn Asp Gly
145                 150                 155                 160

Lys Leu Glu Leu Thr Glu Met Ala Arg Leu Leu Pro Val Gln Glu Asn
                165                 170                 175

Phe Leu Leu Lys Phe Gln Gly Ile Lys Met Cys Gly Lys Glu Phe Asn
            180                 185                 190

Lys Ala Phe Glu Leu Tyr Asp Gln Asp Gly Asn Gly Tyr Ile Asp Glu
        195                 200                 205

Asn Glu Leu Asp Ala Leu Leu Lys Asp Leu Cys Glu Lys Asn Lys Gln
210                 215                 220

Asp Leu Asp Ile Asn Asn Ile Thr Thr Tyr Lys Lys Asn Ile Met Ala
225                 230                 235                 240

Leu Ser Asp Gly Gly Lys Leu Tyr Arg Thr Asp Leu Ala Leu Ile Leu
                245                 250                 255

Cys Ala Gly Asp Asn
            260

<210> SEQ ID NO 3
<211> LENGTH: 5
<212> TYPE: PRT
<213> ORGANISM: Artificial Sequence
<220> FEATURE:
<223> OTHER INFORMATION: Conserved cysteine protease motif
<220> FEATURE:
<221> NAME/KEY: MISC_FEATURE
<222> LOCATION: (4)..(4)
<223> OTHER INFORMATION: "Xaa" denotes either Arginine or Glutamine.

<400> SEQUENCE: 3

Gln Ala Cys Xaa Gly
1               5

<210> SEQ ID NO 4
<211> LENGTH: 4
<212> TYPE: PRT
<213> ORGANISM: Artificial Sequence
<220> FEATURE:
<223> OTHER INFORMATION: Cell-permeable caspase-3 inhibitor.
<220> FEATURE:
<221> NAME/KEY: MISC_FEATURE
<222> LOCATION: (4)..(4)
<223> OTHER INFORMATION: Asp is modified with an aldehyde.

<400> SEQUENCE: 4

Asp Glu Val Asp
1
```

CALBINDIN-$D_{28K}$ PROTECTION AGAINST GLUCOCORTICOID INDUCED CELL DEATH

INTRODUCTION

This application is a continuation-in-part of U.S. Ser. No. 10/155,567 filed May 23, 2002 now abandoned.

This invention was made with government support by the following National Institute of Health Grant DK38961. The government may own certain rights in the present invention.

FIELD OF THE INVENTION

The present invention relates to the fields of molecular biology, gene therapy, and the regulation of apoptosis. In particular, this invention provides a novel mechanism for regulating cell death. Specifically, the present invention is based on the determination that a novel composition containing calbindin-$D_{28K}$ can be administered to a subject to inhibit glucocorticoid induced apoptosis in osteoblastic cells. Thus, the compositions and methods of the present invention are useful for the treatment of such diseases as Glucocorticoid induced osteoporosis, which is the third most prevalent form of osteoporosis.

BACKGROUND OF THE INVENTION

Various publications or patents are referred to throughout this application or at the end of this specification to describe the state of the art to which the invention pertains. Each of these publications or patents is incorporated by reference herein. Citations of scientific publications are set forth in the text or at the end of the specification.

Control of cell numbers in mammals is determined, in part, by a balance between cell proliferation and cell death. Cell death involves processes that are equal in complexity and regulation to those involved in cell proliferation. There are two forms of cell death. One form of cell death is referred to as necrotic cell death. It is typically characterized as a pathologic form of death resulting from cellular trauma or injury. Necrosis is a process that involves loss of membrane integrity and uncontrolled release of cellular contents, giving rise to inflammatory responses. In necrotic cell death, the cell has a passive role in initiating the process of death, it is a response to pathologic changes initiated outside of the cell that results in a change in the plasma membrane permeability that results in cellular edema and the osmotic lysis of the cell. In contrast, the other form of cell death, referred to as apoptosis, usually proceeds in an orderly or controlled manner wherein the cell undergoes an energy-dependent process of cellular death initiated by specific signals in an otherwise normal microenvironment (see, e.g., Barr, et al., Bio/Technology, 12:487-493 (1994); Steller, et al., Science, 267:1445-1449 (1995)).

Apoptosis, or programmed cell death, is a natural 'physiologic' process that occurs during growth and development, and it is an important regulator of tissue homeostasis and aging. It is the process, whereby organisms eliminate unwanted cells to prevent uncontrolled cell proliferation and or disease. Early on in development apoptosis plays a central role in sculpting the fetal animal, precisely managing cell number in tissues and controlling the formation of organs. In homeostasis, apoptosis regulates cell number, facilitates morphogenesis, removes harmful or otherwise abnormal cells, eliminates cells that have already performed their function, and hence, plays a crucial role in the development and maintenance of multicellular organisms by eliminating superfluous or unwanted cells. It further serves as a defense mechanism to remove potentially dangerous cells, including virus-infected cells, self-reactive lymphocytes in autoimmune diseases, or malignant cells and may minimize the risk of developing potentially cancerous cells in tissues frequently exposed to mutagenic chemicals, carcinogens, or UV radiation.

For instance, recent evidence has demonstrated that the rate of bone formation is regulated not only by the rate of osteoblast formation but also by the rate of osteoblast apoptosis. Thus, increased osteoblast apoptosis is at least partially responsible for the reduced bone formation in glucocorticoid excess-induced osteopenia (Weinstein, R. S., Jilka, R. L., Parfitt, A. M., and Manolagas, S. C. (1998) *J. Clin. Invest.* 102, 274-282). Conversely, inhibition of osteoblast apoptosis is a likely mechanism of the anabolic effect of intermittent administration of parathyroid hormone (Jilka, R. L., Weinstein, R. S., Bellido, T., Roberson, P. K., Parfitt, A. M., and Manolagas, S. C. (1999) *J. Clin. Invest.* 104, 439-446).

The programmed cell death process is often associated with characteristic morphological and biochemical changes. Once committed to apoptosis, cells undergo new rounds of protein synthesis and various morphological and physiological changes. The morphological characteristics of apoptosis include organelle re-localization and compaction, cell shrinkage (condensation of nuclear chromatin, nucleoplasm and cytoplasm), the appearance of membrane ruffling, plasma and nuclear membrane blebbing and formation of apoptotic bodies (membrane enclosed particles containing intracellular material), and loss of cell-cell contact followed by fragmentation. Signals for apoptosis promote the activation of specific calcium- and magnesium-dependent endonucleoases that cleave the double stranded DNA at linker regions between nucleosomes. At the end of the process, the phospholipid phosphatidylserine, which is normally hidden within the plasma membrane, is exposed on the cell's surface and bound by neighboring epitheliel cells, macrophages and dendritic cells that engulf and phagocytose the fragments from the apoptotic cell before lysis. In this way, dead cells are removed in an orderly manner without any leakage of their noxious and potentially proinflammatory contents. Because of this clearance mechanism, inflammation is not induced despite the clearance of great numbers of cells. By contrast, during the pathological form of cell death referred to above as necrosis, the mitochondria within the cell swell, lose their function and are rapidly lysed, thereby releasing cytoplasmic contents that invariably trigger an inflammatory response.

In general, the apoptosis cycle can be divided into three phases: an initiation phase in which the various death stimuli take so-called "private" pathways to converge on a common effector phase involving the caspase family of proteins, which leads finally to the degradation phase characterized by the typical biochemical symptoms of cell death. In phase one, the cell undergoes genetic reprogramming in which certain genes that were previously expressed are now repressed, while other genes that were previously repressed are now expressed. These genetic changes result in the activation of double-stranded DNA fragmentation during the next phase.

During phase two, the effector phase, the nuclear morphology changes (i.e., nuclear condensation of chromatin), while the plasma and lysosomal membranes remain intact and the mitochondria continue to function. This phase is regulated by the mitochondrial permeability transition pore since its open or closed conformations determine the fate of the cells. It participates in regulating the level of calcium, the pH and the transmembrane potential in the mitochondria. It has been demonstrated that opening of the pore, regulated by Bcl-2, is a critical event in the process leading to apoptosis as it allows dissipation of the transmembrane potential, disrupting the integrity of the outer membrane and leading to the release of mitochondrial intermembrane proteins, such as cytochrome c (Kroemer et al. 1997).

Subsequently in phase three, proteases are activated, like proteases that hydrolyzes poly(ADP-ribose) polymerase, the lamins in the nuclear membrane are degraded and the nucleus itself undergoes fragmentation. Plasma membrane blebbing and eventual cellular fragmentation into clusters of membrane-bound apoptotic bodies then occurs. Once formed, these apoptotic bodies are rapidly recognized, phagocytized, and digested by macrophages or by adjacent epithelial cells.

Once initiated apoptosis leads to a cascade of biochemical and morphological events that result in irreversible degradation of the genomic DNA and fragmentation of the cell. Entry into this programmed cell death pathway is regulated by a careful balancing act between those specific gene products that promote and those that inhibit apoptosis. A cell activates its internally encoded suicide program as a result of either internal or external signals. In a healthy cell, the protein Bcl-2 is expressed on the outer membrane surface of mitochondria and bound to an Apoptosis Activation Factor-1 (Apaf-1) protein. When a cell undergoes internal damage, Bcl-2 is caused to release Apaf-1 resulting in the disruption of the mitochondria membrane and the leakage of both Apaf-1 and cytochrome c out of the mitochondria. Once released cytochrome c and Apaf-1 bind to a caspase 9 protease to form a complex called an apoptosome, which aggregates in the cytosol. Caspase 9 is thus activated, which in turn activates other members of the caspase family of proteases which results in the digestion of the structural proteins of the cytoplasm, the degradation of chromosomal DNA and ultimately in the phagocytosis of the cell.

Endogenous activation of apoptosis occurs due to the positive presence of a tissue-specific external signal (such as TNF-α or glucocorticoids) that induces cells to self-destruct. One characteristic of the tumor necrosis factor (TNF) family is the ability of many family members to induce programmed cell death in a variety of cells, both normal and of tumor origin (Wiley et al, Immunity 3:673-682, 1995, and references therein). TNF is a cytokine that has been implicated in cell death. There are two forms of TNF, they are the α and β forms. TNF-α is a soluble homotrimer of 17 kD protein subunits. A membrane-bound 26 kD precursor form of TNF-α also exists. TNF α and β are produced from various cells, including, for example, T cells, monocytes, macrophages, and natural killer cells, by induction with prophiogistic agents such as bacteria, viruses, various mitogens or the like.

TNF elicits a broad range of biological effects through two distinct membrane receptors, TNF R1 and TNF R2, which are expressed at low levels on most cell types. Endotoxins strongly activate monocyte/macrophage production and secretion of TNF. It is a mediator of the metabolic and neurohormonal responses to endotoxins. TNF causes the pro-inflammatory actions that result from tissue injury, increases the adherence of neutrophils and lymphocytes, and stimulates the release of platelet activating factor from macrophages, neutrophils and vascular endothelial cells. To this extent, TNF is a key component in biological activities such as inducing hemorrhagic necrosis in tumors, apoptosis in cancer cells, production of prostaglandins and collagenase, expression of adhesion. molecules (ICAM-1, ELAM-1) and HLA class II molecules, production of inflammatory cytokines (e.g., IL-I, IL-6) and chemokines (IL-8, RANTES), and enhancement of absorption of bone and cartilage.

One of the most striking features of TNF compared to other cytokines is its ability to elicit programned cell death. Apoptosis induced by TNF is mediated primarily through TNF R1. The intracellular domain of TNF R1 contains a "death domain" of approximately 80 amino acids that is responsible for signaling cell death by the receptor. When TNF a binds to its integral membrane receptor (TNF R1) a signal is transmitted to the cytoplasm activating caspase 8, which initiates an expanding cascade of sequential caspase family activation and proteolytic activity that results in the eventual phagocytosis of the cell.

Along those lines, it was determined that the inflammatory cytokine TNF, which inhibits bone formation, collagen synthesis, and alkaline phosphatase (Stashenko, P., Obernesser, M. S., and Dewhirst, F. E. (1989) *Immunol. Invest.* 18, 239-249; and Centrella, M., McCarthy, T. L., and Canalis, E. (1988) *Endocrinology* 123, 1442-1448), also induces apoptosis of osteoblastic cells (Jilka, R. L., Weinstein, R. S., Bellido, T., Parfitt, A. M., and Manolagas, S. C. (1998) *J. Bone Miner. Res.* 13, 793-802; Hill, P. A., Tumber, A., and Meikle, M. C. (1997) *Endocrinology* 138, 3849-3858; and Kitajima, I., Nakajima, T., Imamura, T., Takasaki, I., Kawahara, K., Okano, T., Tokioka, T., Soejima, Y., Abeyama, K., and Maruyama, I. (1996) *J. Bone Miner. Res.* 11, 200-210). However, it was further determined that growth factors such as insulin-like growth factor I, basic fibroblast growth factor, interleukin-6 type cytokines, and transforming growth factor inhibit osteoblastic cell apoptosis induced by TNF, serum deprivation, or activation of Fas (Jilka, R. L., Weinstein, R. S., Bellido, T., Parfitt, A. M., and Manolagas, S. C. (1998) *J. Bone Miner. Res.* 13, 793-802; Hill, P. A., Tumber, A., and Meikle, M. C. (1997) *Endocrinology* 138, 3849-3858; and Kitajima, I., Nakajima, T., Imamura, T., Takasaki, I., Kawahara, K., Okano, T., Tokioka, T., Soejima, Y., Abeyama, K., and Maruyama, I. (1996) *J. Bone Miner. Res.* 11, 200-210).

Interestingly, insulin growth factor I and fibroblast growth factor induce the calcium binding protein calbindin-$D_{28K}$ expression in neurons and promote neuronal survival (Collazo, D., Takahashi, H., and McKay, R. D. (1992) *Neuron* 9, 643-656; Nieto-Bona, M. P., Busiguina, S., and Torres-Alemañ, I. (1995) *J. Neurosci. Res* 42, 371-376; Mattson, M. P., Murrain, M., Guthrie, P. B., and Kater, S. B. (1989) 1 *Neurosci.* 9, 3728-3740; and Cheng, B. and Mattson, M. P. (1992) *J. Neurosci.* 12, 1558-1566). Recent evidence suggests the involvement of apoptosis in the regulation of osteoblastic bone formation and osteoclastic bone resorption during adult bone remodeling (Hughes, D. E., and Boyce, B. F. (1997) *J. Clin. Pathol (Lond.)* 50, 132-137; and Manolagas, S. C. ((1999) *Endocrinology* 140, 4377-4381). Because of these facts the inventor set out to determine whether expression levels of calbindin-$D_{28K}$ had an effect on apoptosis of osteoblastic cells. The results showed TNF induced nuclear fragmentation of MC3T3-E1 cells transfected with an empty vector, but that this pro-apoptotic effect of TNF was significantly attenuated in cells transfected with calbindin-$D_{28K}$ cDNA. Hence, it was determined that calbindin-$D_{28K}$ transfectants were resistant to TNT-induced apoptosis.

Since some evidence indicated a role for calcium in the initiation as well as in the degradation phase of apoptosis, it was suggested that the anti-apoptotic effect of calbindin-$D_{28K}$ could be due to its ability to chelate calcium. It was also suggested that calbindin-$D_{28K}$ could inhibit the release of cytochrome c from the mitochondria, which is needed for the activation of caspase-3, by preventing calcium mediated apoptotic damage of mitochondrial electron transport (Guo, Q., Christakos, S., Robinson, N., and Mattson, M. P. (1998) *Proc. Natl. Acad. Sci. U S. A.* 95, 3227-3232). Because recent evidence indicates that the caspase family of proteins play a role in inducing TNF evoked apoptosis it was suggested that calbindin-$D_{28K}$ may interact with one or more of the caspase family of proteases to inhibit apoptosis.

The caspases, are a family of cysteine proteases that share the characteristic feature of a conserved QAC(R/Q)G motif (SEQ ID NO:3), in which the Cys residue is part of the active site and is essential for caspase-mediated apoptosis. These proteases are primarily responsible for the degradation of cellular proteins that lead to the morphological changes seen in cells undergoing apoptosis. It has been shown that many members of the family are capable of inducing apoptosis when overexpressed in mammalian cells (Henkart, 1996 and Miura et al., Cell 75:653 [1993]). For instance, it is known that caspase 1 (interleukin 1β converting enzyme or ICE) is responsible for the activation of interleukin-1β (IL-1β) and is necessary for apoptosis. It is a substrate-specific cysteine protease that cleaves the inactive prointerleukin-1 to produce the mature IL-1. IL-1 is a cytokine involved in mediating a wide range of biological responses including inflammation, septic shock, wound healing, hematopoiesis and growth of certain leukemias and apoptosis. When caspase 1 is overexpressed cell apoptosis can be induced. Over expression of caspases 2 and 3 in fibroblasts and neuroblastoma cells also results in cell death by apoptosis.

Caspase 3 is a protein also known to be intimately involved with a cell's ability to induce apoptosis in normal nuclei. Caspase 3 normally exists in the cytosolic fraction of cells as a 32 kDa inactive precursor that is converted proteolytically to a 20 kDa and a 10 kDa active heterodimer when cells are signaled to undergo apoptosis (Schlegel, et al., Biol. Chem. 271:1841-1844, (1996); Wang, et al., EMBO J. 15:1012-1020, (1996)). And it is known that Bcl-2, prevents the activation of caspase-3 by blocking the mitochondria from releasing cytochrome c, a necessary co-factor for caspase-3 activation (Liu, et al., Cell 86:147-157, (1996); Yang, et al., Science 275:1129-1132, (1997); Kluck, et al., Science 275: 1132-1136, (1997)).

Another extrinsic signal that can trigger apoptosis comes from glucocorticoid hormones. Glucocorticoids exert several effects in tissues that have receptors for them. By binding to their receptors, glucocorticoids regulate the expression of several genes either positively or negatively, in a direct or indirect manner, and are known to arrest cell growth and can induce cell death.

The human glucocorticoid receptor is made up of 777 amino acids and is predominantly cytoplasmic in its unactivated, non-DNA binding form. When activated, it translocates to the nucleus. There are four major functional domains of the glucocorticoid receptor. The first, from the amino terminal, is the tau I domain, which spans amino acid positions 77-262 and regulates gene activation. The second is the DNA binding domain, which spans amino acid positions 421-486 and contains nine cysteine residues, eight of which form two different zinc fingers. The DNA binding domain binds to the regulatory sequences of genes that are induced (or deinduced) by glucocorticoids. The tau 2 domain runs from amino acids 532-555 and it is also important for transcriptional activation. Towards the carboxyl terminal end, from amino acids 555 to 777, is the steroid binding domain, which binds glucocorticoid to activate the receptor. This region of the receptor also has the nuclear localization signal.

The glucocorticoid receptor is expressed in the cytoplasm of a cell. When a glucocorticoid enters a cell and binds its receptor, the receptor goes through a conformational change wherein it is activated, forms a heterodimer with another glucocorticoid bound receptor. complex and is transported via a transport protein to the nucleus of the cell. This heterodimer complex interacts with the cell's DNA upregulating the production of the pro-apoptotic signal:bax. The bax protein is transported to the surface membrane of a mitochondria wherein it forms a pore, causing the release of cytochrome c, which then binds to the Apaf-1 protein resulting in the activation of the caspase cascade and phosphatidyl serine being displayed, which leads to the engulfment and degradation of the cell by neighboring epithelial and macrophage cells.

As stated above, signals that initiate apoptosis trigger the so-called private pathways of death, which are specific for particular groups of stimuli and lead to the conversion of procaspases to active the caspases. Although both TNT a and the glucocorticoid hormones can induce apoptosis by binding to their respective receptors and activating the caspase family cascade, little is known about the actual signaling events that occur once the caspases are activated, nor what caspases are activated and by which inducer, nor which lead to the common cell death pathway. The end result of this cascade, however, is chromatin condensation, nuclear fragmentation, increase in cell membrane permeability, and ultimately cell death (Thornberry, N. A., and Lazebnik, Y. (1998) Science 281, 1312-1316; and Green, D. R. (1998) Cell 94, 695-698).

The inventor's previous work establishes a relationship between calbindin-$D_{28K}$ and caspase-3 in that it was determined that calbindin-$D_{28K}$ could prevent TNF induced apoptosis by interacting with caspase-3 via an unknown mechanism. (See Bellido et al. (2000) Journal of Biol. Chem. 275, 26326-26332.) The present work of the inventor, and the subject matter of the present invention establishes that calbindin-$D_{28K}$ can also prevent glucocorticoid induced cell death. Given that apoptosis is tightly regulated and has been linked to pathways that are dysregulated in a variety of diseases including cancer, the present invention is important because it further elucidates a mechanism by which to control this process, especially as it relates to glucocorticoid induced cell death. For instance, the compositions and methods of the present invention are useful in the prevention and treatment of glucocorticoid induced osteoporosis, which is the third most prevalent form of osteoporosis after postmenopause and senile osteoporosis.

SUMMARY OF THE INVENTION

The present invention provides novel compositions containing a calbindin-$D_{28K}$ therapeutic element, which is involved in the regulation of apoptosis, and may be administered for the prevention of an abnormal apoptosis response in cells. In particular the compositions and methods of the present invention may be used for the prevention or induction of apoptosis in such cells types as osteoblasts and osteocytes. Specifically, the compositions and methods of the present invention may be useful in the prevention of glucocorticoid induced cell death in osteoblasts and the treatment of such conditions as glucocorticoid induced osteoporosis.

According to one aspect, this invention depends on an isolated polynucleotide encoding a calbindin-$D_{28K}$ protein. Preferably, the polynucleotide comprises the sequence of: SEQ ID NO:1, with up to 30% conservative substitutions; an allelic variant of SEQ ID NO:1; a sequence hybridizing with SEQ ID NO:1 or its complement under moderate hybridization and washing conditions, or an antisense sequence to SEQ ID No:1. Further, in another aspect, this invention depends on an isolated polypeptide sequence having an amino acid sequence of SEQ ID NO:2 with up to 30% conservative substitutions.

Specifically, one aspect of the invention features a recombinant calbindin-$D_{28K}$ DNA or RNA molecule comprising a vector having an insert that includes part or all of a calbindin- $D_{28K}$ polynucleotide, or its antisense polynucleotide sequence. The invention also features a vector containing a calbindin-$D_{28K}$ polypeptide. Pharmaceutical compositions containing a biologically effective amount of the calbindin-$D_{28K}$ polynucleotide, antisense sequence, protein and/or protein fragments with acceptable carriers are also provided.

Hence, in another, particular embodiment, the present invention may be implicated in the treatment of diseases and conditions such as increased cell death in such cells as osteoblasts and osteocytes. Therefore, the invention relates to compositions and methods for treating diseased conditions associated with an abnormal increase in apoptosis, by administering a calbindin-$D_{28K}$ gene or protein to decrease programmed cell death. Specifically, a method of treating a disease associated with abnormal glucocorticoid induced cell death involving the administration of a pharmaceutical composition containing a biologically effective amount of a calbindin-$D_{28K}$ polynucleotide or polypeptide along with an acceptable carrier, is provided.

Further, in another particular embodiment, the present invention may be implicated in the treatment of diseases and conditions associated with decreased apoptosis such as various bone osteoblastic cancers. Therefore, the invention relates to compositions and methods for treating diseased conditions associated with an abnormal decrease in apoptosis, by administering a pharmaceutical composition containing a biologically effective amount of a calbindin-$D_{28K}$ antisense sequence along with an acceptable carrier, downregulating the endogenous production of the calbindin-$D_{28K}$ protein, especially in osteoblast or osteocyte cells with an abnormal growth rate, and thereby increasing the likelihood of apoptosis and thus the killing off of the cell without evoking an immune response. This mechanism may also be useful in other cells wherein endogenous calbindin-$D_{28K}$ is produced, such as various cells of the prostate.

Specifically, in a particular embodiment, the invention relates to the administration of vectors for the delivery of a calbindin-$D_{28K}$ therapeutic element to a cell for the treatment of diseases associated with an abnormal increase or decrease in cell death, wherein the vector contains an expression cassette encoding the calbindin-$D_{28K}$ therapeutic. The calbindin-$D_{28K}$ therapeutic can be a calbindin-$D_{28K}$ polynucleotide, a calbindin-$D_{28K}$ polynucleotide antisense sequence, a calbindin-$D_{28K}$ protein, or a calbindin-$D_{28K}$ protein fragment. The expression cassette may contain one or more of the following elements: a host cell origin of replication, a suitable promoter operably linked to a heterologous genetic element, an internal ribosome entry site, splice donor site, splice acceptor site, a suitable enhancer, PPT track, heterologous genetic element, a reporter gene, and/or an appropriate termination sequence. One or more of these vectors, containing a calbindin-$D_{25}k$ therapeutic, may be introduced into an appropriate cell by a variety of means, including in vivo, in vitro or ex vivo transduction or transfection using an appropriate expression system.

BRIEF DESCRIPTION OF THE DRAWINGS

The invention is best understood from the following detailed description when read in connection with the accompanying drawings, in which.

DETAILED DESCRIPTION OF THE INVENTION

In light of the recent work by the Applicant calbindin-$D_{28K}$ has been identified as a protein that can regulate glucocorticoid induced cell death in various cell types, but particularly in osteoblast and osteocyte cells. By binding caspase 3, calbindin-$D_{28K}$ inhibits the ability of caspase 3 to proteolytically cleave, thereby inhibiting its function and preventing glucocorticoid induced cell death and therefore, osteoporosis.

Although specific embodiments of the present invention will now be described, it should be understood that such embodiments are by way of example only and merely illustrative of but a small number of the many possible specific embodiments that can represent applications of the principles of the present invention. Various changes and modifications obvious to one skilled in the art to which the present invention pertains are deemed to be within the spirit, scope and contemplation of the present invention as further defined in the appended claims.

DEFINITIONS

Various terms relating to the biological molecules of the present invention are used throughout the specification and claims.

"Calbindin-$D_{28K}$" refers generally to a calbindin-$D_{28K}$ polypeptide that has been found to regulate glucocorticoid induced cell death by inhibiting the ability of caspase 3 to proteolytically cleave, and thereby preventing glucocorticoid induced osteoporosis, in accordance with the present invention, which is described in detail herein above and throughout the specification.

"Calbindin-$D_{28K}$ activity or calbindin-$D_{28K}$ polypeptide activity" or "biological activity of the calbindin-$D_{28K}$ protein or calbindin-$D_{28K}$ polypeptide" refers to the metabolic or physiologic function of said calbindin-$D_{28K}$ including similar activities or improved activities or these activities with decreased undesirable side effects. In particular, the calbindin-$D_{28K}$ polynucleotide encodes a protein that interacts with caspase-3 in such a way as to inhibit glucocorticoid induced cell death.

"Calbindin-$D_{28K}$ gene" refers to a polynucleotide in accordance with the present invention, which encodes a calbindin-$D_{28K}$ polypeptide.

A "calbindin-$D_{28K}$ therapeutic" refers to a therapeutically effective amount of a calbindin-$D_{28K}$ related genetic sequence such as, but not limited to polynucleotide, polynucleotide antisense sequence, and calbindin-$D_{28K}$ peptide, protein or protein fragment.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RINA or DNA or both RNA and DNA.

The term polynucleotide also includes DNAs or RNAs containing one or more -modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the gene-encoded amino acids. "Polypeptides" include amino acid sequences modified either by natural processes, such as posttranslational processing, or by chemical modification techniques that are well known in the art. Such modifications are well described in basic texts and in more detailed monographs; as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods.

Modifications include acetylation, acylation, ADP-ribosylation, amidation, covalent attachment of various moiety groups, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross links, formation of cystine, formation of pyroglutamate, formylation, gamma-carboxylation, glycosylation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, Proteins—Structure And Molecular Properties, 2nd Ed., T. E. Creighton, W. H. Freeman and Company, New York, 1993 and Wold, F., "Posttranslational Protein Modifications: Perspectives and Prospects, pgs. 1-12 in "Posttranslational Covalent Modification Of Proteins", B, C. Johnson, Ed., Academic Press, New York, 1983; Seifter et al., "Analysis for protein modifications and nonprotein cofactors", Meth Enzymol (1990) 182:626-646 and Rattan et al., "Protein Synthesis: Posttranslational Modifications and Aging", Ann AIYAcad Sci (1992) 663:48-62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polyriucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical.

A variant and reference polypeptide may differ in amino acid sequence by one or more substitutions, additions, and deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis. For instance, a conservative amino acid substitution may be made with respect to the amino acid sequence encoding the polypeptide.

A "conservative amino acid substitution", as used herein, is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The term "substantially the same" refers to nucleic acid or amino acid sequences having sequence variation that do not materially affect the nature of the protein (i.e. the structure, stability characteristics, substrate specificity and/or biological activity of the protein). With particular reference to nucleic acid sequences, the term "substantially the same" is intended to refer to the coding region and to conserved sequences governing expression, and refers primarily to degenerate codons encoding the same amino acid, or alternate codons encoding conservative substitute amino acids in the encoded polypeptide. With reference to amino acid sequences, the term "substantially the same" refers generally to conservative substitutions and/or variations in regions of the polypeptide not involved in determination of structure or function.

With respect to single-stranded nucleic acid molecules, the term "specifically hybridizing" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule, to the substantial exclusion of hybridization of the oligonucleotide with single-stranded nucleic acids of non-complementary sequence.

With respect to oligonucleotide constructs, but not limited thereto, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide construct with a substantially complementary sequence contained within a single-stranded DNA or RNA molecule of the invention, to the substantial exclusion of hybridization of the oligonucleotide with single-stranded nucleic acids of non-complementary sequence.

The term "substantially pure" refers to a "preparation comprising at least 50-60% by weight the compound of interest (e.g., nucleic acid, oligonucleotide, protein, etc.). More preferably, the preparation comprises at least 75% by weight, and most preferably 90-99% by weight, the compound of interest. Purity is measured by methods appropriate to the compound of interest (e.g. chromatographic methods, agarose or polyacrylamide gel electrophoresis, HPLC analysis, and the like).

The term "expression cassette" refers to a nucleotide sequence that contains at least one coding sequence along with sequence elements that direct the initiation and termination of transcription. An expression cassette may include additional sequences, including, but not limited to promoters, enhancers, sequences involved in post-transcriptional or post-translational processes, as well as appropriate terminator sequences.

A "coding sequence" or "coding region" refers to a nucleic acid molecule having sequence information necessary to produce a gene product, when the sequence is expressed.

The term "operably linked" or "operably inserted" means that the regulatory sequences necessary for expression of the coding sequence are placed in a nucleic acid molecule in the appropriate positions relative to the coding sequence so as to enable expression of the coding sequence. This same definition is sometimes applied to the arrangement of other transcription control elements (e.g., enhancers and regulators) in an expression vector.

Transcriptional and translational control sequences are DNA regulatory sequences, such as promoters, enhancers, polyadenylation signals, terminators, and the like, that provide for the expression of a coding sequence in a host cell.

The terms "promoter", "promoter region" or "promoter sequence" refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is-bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease 51), as well as protein binding domains (consensus sequences) responsible for the binding of RNA polymerase.

The term "nucleic acid construct" or "DNA construct" is sometimes used to refer to a coding sequence or sequences operably linked to appropriate regulatory sequences and inserted into a vector for transforming a cell, in vitro or in vivo. This term may be used interchangeably with the term "transforming DNA". Such a nucleic acid construct may contain a coding sequence for a gene product of interest, along with a selectable marker gene and/or a reporter gene.

A "heterologous" region of a nucleic acid construct is an identifiable segment (or segments) of the nucleic acid molecule within a larger molecule that is not found in association with the larger molecule in nature. Thus, when the heterologous region encodes a mammalian gene, the gene will usually be flanked by DNA that does not flank the mammalian genomic DNA in the genome of the source organism. In another example, a heterologous region is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

The term "DNA construct", as defined above, is also used to refer to a heterologous region, particularly one constructed for use in transformation of a cell. A cell has been "transformed" or "transfected" or "transduced" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA.

The term "in vivo delivery" involves the use of any gene delivery system, such as viral- and liposome-mediated transformation for the delivery and introduction of a therapeutic agent to the cells of a subject while they remain in the subject. Such therapeutic elements may include, for example, calbindin-$D_{28K}$ DNA, eDNA, RNA, and antisense polynucleotide sequences.

As used herein, the term "transduction," is used to describe the delivery of DNA to eukaryotic cells using viral mediated delivery systems, such as, adenoviral, AAV, retroviral, or plasmid delivery gene transfer methods. Preferably the viral mediated delivery system is targeted specificaldly to the cell, wherein delivery is sought. The production of targeted delivery systems is well known and practiced in the recombinant arts. A number of methods for delivering therapeutic formulations, including DNA expression constructs (as described further below), into eukaryotic cells are known to those skilled in the art. In light of the present disclosure, the skilled artisan will be able to deliver the therapeutic elements of the present invention to cells in many different but effective ways. Naturally, different viral host ranges will dictate the virus chosen for gene transfer.

"In vitro gene delivery" refers to a variety of methods for introducing exogenous DNA into a cell that has been removed form its host environment.

As used herein the term, "transfection" is used to describe the delivery and introduction of a therapeutic agent to a cell using non-viral mediated means, these methods include, e.g., calcium phosphate- or dextran sulfate-mediated transfection; electroporation; glass projectile targeting; and the like. These methods are known to those of skill in the art, with the exact compositions and execution being apparent in light of the present disclosure.

"Ex vivo gene delivery" refers to the procedure wherein appropriate cells are removed form the host organism, transformed, transduced or transfected in accordance with the teachings of the present invention, and replaced back into the host organism, for the purpose of therapeutic restoration and/or prevention.

"Delivery of a therapeutic element or agent" may be carried out through a variety of means, such as by using parenteral delivery methods such as intravenous and subcutaneous injection, and the like. Such methods are known to those of skill in the art of drug delivery, and are further described herein in the sections regarding pharmaceutical preparations and treatment. Compositions, include pharmaceutical formulations, comprising a calbindin-$D_{28K}$ gene, protein, or antisense polynucleotide sequence that may be delivered. In such compositions, the calbindin-$D_{28K}$ may be in the form a DNA segment, plasmid, recombinant vector or recombinant virus that is capable of expressing a calbindin-$D_{28K}$ protein in a cell; specifically, an osteoblast cell. These compositions, including those comprising a recombinant viral gene delivery system, such as an adenovirus particle, may be formulated for in vivo administration by dispersion in a pharmacologically acceptable solution or buffer. Preferred pharmacologically acceptable solutions include neutral saline solutions buffered with phosphate, lactate, Tris and the like.

The term "contacted" when applied to a cell is used herein to describe the process by which a calbindin-$D_{28K}$ genetic element, such as a gene, protein or antisense sequence is delivered to a target cell or is placed in direct proximity with the target cell. This delivery may be in vitro or in vivo and may involve the use of a recombinant vector system. Any method may be used to contact a cell with the calbindin-$D_{28K}$ associated protein or nucleotide sequence, so long as the method results in either increased or decreased levels of functional calbindin-$D_{28K}$ protein within the cell. This includes both the direct delivery of a calbindin-$D_{28K}$ protein to the cell and the delivery of a gene or DNA segment that encodes calbindin-$D_{28K}$, or its antisense polynucleotide sequence, which gene or antisense sequence will—direct or inhibit, respectfully, the expression and production of calbindin-$D_{28K}$ within the cell. Since protein delivery is subject to drawbacks, such as degradation and low cellular uptake, it is contemplated that the use of a recombinant vector that expresses a calbindin-$D_{28K}$ protein, or encodes for a calbindin-$D_{28K}$ polynucleotide antisense sequence, will be of particular advantage for delivery.

With respect to "therapeutically effective amount" is an amount of the polynucleotide, antisense polynucleotide or protein of calbindin-$D_{28K}$, or fragment thereof, that when administered to a subject is effective to bring about a desired effect (e.g., an increase or decrease of apoptosis) within the subject.

Polynucleotides

The present invention provides a novel composition containing a therapeutic calbindin-$D_{28K}$ genetic element, such as a gene or protein, which acts as a mediator of glucocorticoid induced apoptosis. The calbindin-$D_{28K}$ gene and protein of the present invention, when introduced to a cell have been found to inhibit glucocorticoid induced cell death. The summary of the invention described above is non-limiting and other features and advantages of the invention will be apparent from the following detailed description.

The present invention concerns compositions and methods for treating various diseases associated with either an unhealthy increase or decrease in programmed cell death. The invention is based firstly on the inventor's discovery that calbindin-$D_{28K}$ protects against dexamethasone, a glucocorticoid, induced cell death. To determine if calbindin-$D_{28K}$ could protect against glucocorticoid induced cell death, Applicant transfected MLO-Y4 osteocytic cells with either a pREP4 calbindin-$D_{28K}$ or BSRα calbindin-$D_{28K}$ expression vector construct and then incubated the cells and dexamethasone. After 6, 12 and 24 hours the cells were assayed to determine characteristic apoptotic morphological changes due to the presence of dexamethasone, and MLO-Y4 cells transfected with the calbindin-$D_{28}$k containing vector were observed to have been protected against glucocorticoid induced cell death over those cells transfected with the naked vector alone. Thus, the inventor discovered that calbindin-$D_{28k}$ plays a role in regulating glucocorticoid induced cell death in bone cells, and maybe useful in the treatment of the various forms of glucocorticoid induced osteoporosis.

As described in detail in Example 1, the calbindin-$D_{28k}$ gene was cloned into two different expression vector constructs, pREP4 and BSRα calbindin-$D_{28k}$. The human calbindin-$D_{28k}$ gene is set out in SEQ ID NO: 1. The calbindin-$D_{28k}$ polynucleotides of the present invention include isolated polynucleotides encoding calbindin-$D_{28k}$ proteins, polypeptides and/or fragments, and polynucleotides closely related thereto. More specifically, calbindin-$D_{28k}$ polynucleotides of the invention include a polynucleotide comprising the human nucleotide sequences contained in SEQ ID NO:1 encoding a calbindin-$D_{28k}$ polypeptide of SEQ ID NO:2, and polynucleotides having the particular sequence of SEQ ID NO: 1.

Calbindin-$D_{28k}$ polynucleotides further include a polynucleotide comprising a nucleotide sequence that has at least 70% identity over its entire length to a nucleotide sequence encoding the calbindin-$D_{28k}$ polypeptide of SEQ ID NO:2, and a polynucleotide comprising a nucleotide sequence that is at least 70% identical to that of SEQ ID NO:1, over its entire length. In this regard, polynucleotides with at least 70% are preferred, more preferably at least 80% even more preferably at least 90% identity, yet more preferably at least 95% identity, 97% are highly preferred and those with at least 98-99% are most highly preferred, with at least 99% being the most preferred.

The present invention includes polynucleotides encoding polypeptides which have at least 70% identity, preferably at least 80% identity, more preferably at least 90% identity, yet more preferably at least 95% identity, even more preferably at least 97-99% identity, to the amino acid sequence of SEQ ID NO:2, over the entire length of the recited amino acid sequences. The nucleotide sequences encoding the calbindin-$D_{28k}$ polypeptide of SEQ ID NO:2 may be identical to the polypeptide encoding sequence contained in SEQ ID NO:1, or it may be a sequence, which as a result of the redundancy (degeneracy) of the genetic code, also encodes the polypeptide of SEQ ID NO:2. Also included under calbindin-$D_{28k}$ polynucleotides are nucleotide sequences that code for polynucleotides that are complementary to such calbindin-D-$D_{28k}$ polynucleotides, such as anti-sense calbindin-$D_{28k}$ polynucleotide sequences.

Calbindin-$D_{28k}$ polynucleotides of the present invention may be prepared by two general methods: (1) they may be synthesized from appropriate nucleotide triphosphates, or (2) they may be isolated from biological sources. Both methods utilize protocols well known in the art. The availability of nucleotide sequence information, such as the cDNA having SEQ ID NO: 1, enables preparation of an isolated nucleic acid molecule of the invention by oligonucleotide synthesis.

Synthetic oligonucleotides may be prepared by the phosphoramadite method employed in the Applied Biosystems 38A DNA Synthesizer or similar devices. The resultant construct may be purified according to methods known in the art, such as high performance liquid chromatography (HPLC). Long, double-stranded polynucleotides, must be synthesized in stages, due to the size limitations inherent in current oligonucleotide synthetic methods. Thus, for example, a long double-stranded molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire long double-stranded molecule. A synthetic DNA molecule so constructed may then be cloned and amplified in an appropriate vector. In this respect, the polynucleotide may also contain non-coding S and 3' sequences, such as transcribed, non-translated sequences, splicing and polyadenylation signals, ribosome binding sites and sequences that stabilize mRNA.

Calbindin-$D_{28k}$ genes may be isolated from appropriate biological sources using methods known in the art. In the exemplary embodiment of the invention, calbindin-$D_{28k}$ may be isolated from genomic libraries of rat kidneys as described in Panalni et al., (1984) *J. Biol. Chem.* 259, 9735-9741. A preferred means for isolating calbindin-$D_{28k}$ genes is PCR amplification using genomic or cDNA templates and calbindin-$D_{28k}$ specific primers. Genomic and cDNA libraries are commercially available, such as those sold by Sigma, and can also be made by procedures well known in the art. In positions of degeneracy where more than one nucleic acid residue could be used to encode the appropriate amino acid residue, all the appropriate nucleic acid residues may be incorporated to create a mixed oligonucleotide population, or a neutral base such as inosine may be used. The strategy of oligonucleotide design is well known in the art. Nucleic acids of the present invention may be maintained as DNA in any convenient cloning vector. In a preferred embodiment, clones are maintained in plasmid cloning/expression vector, such as pBluescript (Stratagene, La Jolla, Calif.), that is propagated in a suitable *E. coli* host cell.

Hence, in one particular aspect, the present invention provides novel compositions containing a calbindin-$D_{28k}$ therapeutic element, which is involved in the regulation of apoptosis, and may be administered for the prevention of an abnormal apoptosis response in cells. More particularly, the invention pertains to novel compositions containing a calbindin-$D_{28k}$ polynucleotide sequence that may be used for the prevention or induction of apoptosis in such cells types as osteoblasts and osteocytes. More particularly still, the polynucleotide compositions and methods of the present invention may be useful in the prevention of glucocorticoid induced cell death in osteoblasts and osteocytes and the treatment of such conditions as glucocorticoid induced osteoporosis.

Specifically, according to one aspect, this invention depends on an isolated polynucleotide encoding a calbindin-$D_{28k}$ protein. Preferably, the polynucleotide comprises the sequence of: SEQ ID NO:1, with up to 30% conservative substitutions; an allelic variant of SEQ ID NO:1; a sequence hybridizing with SEQ ID NO:1 or its complement under moderate hybridization and washing conditions, or an antisense sequence to SEQ ID NO:1. In a particular preferred embodiment, a pharmaceutical composition containing a therapeutically effective amount of a calbindin-$D_{28k}$ polynucleotide along with a biologically acceptable carrier is provided, where by the administration of said composition will be useful for the prevention and/or treatment of glucocorticoid induced osteoporosis.

Polypeptides

In one aspect, the present invention relates to calbindin-$D_{28k}$ polypeptides, calbindin-$D_{28k}$ proteins, or therapeutically active fragments thereof The calbindin-$D_{28k}$ polypeptides include the polypeptide of SEQ ID NO:2; as well as polypeptides comprising the amino acid sequence of SEQ ID NO:2; and polypeptides comprising the amino acid sequences that have at least 70% identity to that of SEQ ID NO:2, over its entire length. Preferably calbindin-$D_{28k}$ polypeptides or proteins exhibit at least one biological activity of calbindin-$D_{28k}$, specifically the ability to interact with the caspase family of proteins to inhibit apoptosis. The present invention further provides for a polypeptide that comprises an amino acid sequence that has at least 80% identity, more preferably at least 90% identity, yet more preferably at least 95% identity, most preferably at least 97-99% identity, to that of SEQ ID NO:2 over the entire length of SEQ ID NO:2.

The calbindin-$D_{28k}$ polypeptides may be in the form of the "mature" protein or may be a part of a larger protein, such as a fusion protein. It is often advantageous to include an additional amino acid sequence which contains secretory or leader sequences, pre/pro-sequences, sequences which aid in purification such as multiple histidine residues, or an additional sequence for stability during recombinant production.

Fragments of the calbindin-$D_{28k}$ proteins are also included in the invention. A fragment is a polypeptide having an amino acid sequence that entirely is the same as part, but not all, of the amino acid sequence of the aforementioned calbindin-$D_{28k}$ polypeptides. Preferred fragments include, for example, truncation polypeptides having the amino acid sequence of calbindin-$D_{28k}$ polypeptides, except for deletion of a continuous series of residues that includes the amino terminus, or a continuous series of residues that includes the carboxyl terminus or deletion of two continuous Series of residues, one including the amino terminus and one including the carboxyl terminus, but having the same functionality as the endogenous calbindin-$D_{28k}$ protein, namely, the ability to interact with the caspase family of protein to inhibit or reduce apoptosis. Other preferred fragments are biologically active fragments. Biologically active fragments are those that mediate ealbindin-$D_{28}k$ activity, including those with a similar activity or an improved activity, or with a decreased undesirable activity. Also included are those that are antigenic or immunogenic in an animal, especially in a human. Preferably, all of these polypeptide fragments retain the biological activity of the calbindin-$D_{28k}$. Variants of the defined sequence and fragments also form part of the present invention. Preferred variants are those that vary from the referents by conservative amino acid substitutions.

The calbindin-$D_{28k}$ proteins and polypeptides of the invention can be prepared in any suitable manner or purchased, recombinantly, from commercial sources such as Swant Swiss Antibodies. If produced in situ, the polypeptides may be purified from appropriate sources, e.g., appropriate vertebrate cells e.g., mammalian cells, for instance cells from human, mouse, bovine or rat. Alternatively, the availability of nucleic acid molecules encoding the polypeptides enables production of the proteins using in vitro expression methods well known in the art. For example, a cDNA or gene may be cloned into an appropriate in vitro transcription vector, for in vitro transcription, followed by cell-free translation in a suitable cell-free translation system. In vitro transcription and translation systems are commercially available, e.g., from Promega Biotech, Madison, Wis., or BRL, Rockville, Md. While in vitro transcription and translation is not the method of choice for preparing large quantities of the protein, it is ideal for preparing small amounts of native or mutant proteins for research purposes, particularly since it allows the incorporation of radioactive nucleotides.

Larger quantities of calbindin-$D_{28k}$ encoded polypeptide may be produced by expression in a suitable prokaryotic or eukaryotic system. For example, part or all of a DNA molecule, such as the coding portion of SEQ ID NO:1 may be inserted into a plasmid vector adapted for expression in a bacterial cell (such as *E. coli*) or a yeast cell (such as *Saccharomyces cerevisiae*). Such vectors comprise the regulatory elements necessary for expression of the DNA in the host cell, positioned in such a manner as to permit expression of the DNA into the host cell. Such regulatory elements required for expression include appropriate origins of replication, promoter sequences, transcription initiation sequences and optionally, enhancer or termination sequences. Secretion signals may be used to facilitate purification of the resulting protein. An appropriate secretion coding sequence for the secretion of the peptide is operably linked to the 5' end of the coding sequence for the protein, and this hybrid nucleic acid molecule is inserted into a plasmid adapted to express the protein in the host cell of choice. Plasmids specifically designed to express and secrete foreign proteins are available from commercial sources. For example, if expression and secretion is desired in *E. coli*, commonly used plasmids include pTrcPPA (Pharmacia); pPROK-C and pKK233-2 (CLONTECH™); and pNH8a; pNH16a, pcDNAII and pAX (Stratagene), among others.

The calbindin-$D_{28k}$ proteins produced by in vitro transcription and translation or by gene expression in a recombinant prokaryotic or eukaryotic system may be purified according to methods known in the art. Recombinant proteins can be purified by affinity separation, such as by immunological interaction with antibodies that bind specifically to the recombinant protein or fusion proteins such as His tags. Such methods are commonly used by skilled practitioners.

Using appropriate amino acid sequence information, synthetic calbindin-$D_{28k}$ proteins of the present invention may be prepared by various synthetic methods of peptide synthesis via condensation of one or more amino acid residues, in accordance with conventional peptide synthesis methods. Preferably, peptides are synthesized according to standard solid-phase methodologies, such as may be performed on an Applied Biosystems Model 430A peptide synthesizer (Applied Biosystems, Foster City, Calif.), according to manufacturer's instructions. Other methods of synthesizing peptides or peptidomimetics, either by solid phase methodologies or in liquid phase, are well known to those skilled in the art. The protein produced may be purified from the cells and directly injected to the BM tissue, infused to osteoblast cells, or delivered in a lyophilized carrier.

Hence, in one particular embodiment, the present invention provides novel compositions containing a calbindin-$D_{28k}$ therapeutic element, specifically a calbindin-$D_{28k}$ polypeptide, protein or protein fragment, which may act as a regulator of apoptosis, and may be administered for the prevention of an abnormal apoptosis response in cells, in particular osteoblasts and osteoclasts. However, it has also been shown that calbindin-$D_{28k}$ can protect against glucocorticoid induced lymphocyte cell death (Dowd. D. P., et al., Stable expression of calbindin-$D_{28k}$ complimentary DNA apoptotic pathway in lymphocytes. Endocrinology 6: 1843-1848, 1992) hence, it is possible that the compositions and methods of the present invention may also be useful for preventing premature or excessive lymphocytic death caused by glucocorticoids.

In particular the calbindin-$D_{28k}$ protein compositions and methods of the present invention may be used for the prevention of apoptosis in such cell types as osteoblasts and osteocytes, as well as lymphocytes. Specifically, the compositions and methods of the present invention may be useful in the prevention of glucocorticoid induced cell death in osteoblasts and the treatment of such conditions as glucocorticoid induced osteoporosis.

According to one specific aspect, this invention depends on an isolated polypeptide encoding a calbindin-$D_{28k}$ protein. Preferably, the polypeptide comprises the amino acid sequence of: SEQ ID NO:2, with up to 30% conservative substitutions. In a particular aspect, the invention relates to compositions and methods for using such polypeptides for treating diseases associated with abnormal or increased programmed cell death, by administering a calbindin-$D_{28k}$ polypeptide, in a pharmaceutically acceptable and appropriate delivery vehicle, to decrease apoptosis.

Vectors, Host Cells, and Expression

In one particular embodiment the present invention relates to vectors that comprise calbindin-$D_{28k}$ therapeutic related genetic elements, such as a polynucleotide or polynucleotides of the present invention and to the production of polypeptides and proteins of the invention by recombinant techniques both in vitro and in vivo, as well as ex vivo procedures. Cell-free translation systems can also be employed to produce such proteins using RNAs derived from the DNA constructs of the present invention.

Host cells can be genetically engineered to incorporate expression systems or portions thereof for polynucleotides of the present invention. In accordance with the methods of the present invention, host cells, such as osteoblasts and/or osteocytes, may also be obtained from the bone marrow of a subject by procedures well known in the medical research arts. Introduction of polynucleotides into host cells can then be effected by methods described in many standard laboratory manuals, such as Davis et al., Basic Methods In Molecular Biology (1986) and Sambrook et al., Molecular Cloning: A Laboratory Manual, 2nd Ed., Cold Spring Harbor Laboratory Press, Cold Spring Harbor, N.Y. (1989). These methods include calcium phosphate transfection, DEAE-dextran mediated transfection, microinjection, cationic lipid-mediated transfection, lipofectamine transfection, electroporation, transduction, scrape loading, ballistic introduction or infection.

Representative examples of appropriate hosts for in vitro procedures include bacterial cells, such as *Streptococci, Staphylococci, E. coli, Streptomyces, Lactobacillus, Bacillus* cells; fungal cells, such as non-pathogenic yeast cells and *Aspergiffits* cells; and animal cells such as CHO, COS, HeLa, C127, 3T3, BHK, HEK 293 and Bowes melanoma cells. The selection of an appropriate host is deemed to be within the scope of those skilled in the art from the teachings herein.

More particularly, the present invention also includes recombinant constructs comprising a calbindin-$D_{28k}$ DNA, cDNA or RNA sequence as well as compliment nucleotide sequences, i.e., for triplexing duplex DNA, and antisense polynucleotide sequences. The construct comprises a vector, such as a plasmid or viral vector, into which the clone has been inserted, in a forward or reverse orientation. In a preferred aspect of this embodiment, the construct further comprises regulatory sequences, including, for example, a promoter, operably linked to the genetic sequence, and may include a suitable origin of replication or termination sequence. Large numbers of suitable vectors and promoters are known to those of skill in the art, and are commercially available. The following vectors are provided by way of example: Bacterial: pQE7O, pQE6O, pQE-9 (Qiagen), pBS, pDlO, phagescript, psiX 174, pbluescript SK, pbsks, pNH8A, pNH 16a, pNHI8A, pNH46A (Stratagene); ptrc99a, pKK223-3, pKK233-3, pDR54O, Prit5 (Pharmacia); Eukaryotic: pWLNEO, pSV2CAT, pOG44, pXTI, pSG (Stratagene) pSVK3, pBPV, pMSG, pSVL (Pharmacia); of particular importance are the pREP4 calbindin-$D_{28k}$ and BSRα calbindin-$D_{28k}$ expression vectors of the present invention. As further examples, calbindin-$D_{28k}$ cDNA may be inserted in the pEF/myc/cyto vector (from Invitrogen) and/or the pCMV-Tag3b vector (from Stratagene), which can then be used with anti-Myc Ab, to transform Stem, HeLa, Osteoblasts (or other) cells with the calbindin-$D_{28k}$ DNA. However, any other plasmid or vector may be used as long as they are replicable and viable in the host.

In addition, a complete mammalian transcription unit and a selectable marker can be inserted into a prokaryotic plasmid for use in in vivo procedures. The resulting vector is then amplified in bacteria before being transfected into cultured mammalian cells, i.e., osteoblasts or delivered directly to the subject with an acceptable biological carrier as described below. Examples of vectors of this type include pTK2, pHyg, pRSVneo, pREP4 or BSRαt. Hence, these plasmids, constructs and vectors may be used in both in vivo and ex vivo procedures. Ex vivo procedures involve the removal of a host cell, such as bone marrow, osteoblast or osteoclast cells, from the subject, recombinant manipulation of the cell (i.e., transformation, transduction or transfection with a suitable calbindin-$D_{28k}$ expression system vector), and the re-delivery of the cell back into its host environment.

A wide variety of recombinant plasmids and delivery methods may be engineered to express the calbindin-$D_{28k}$ protein and used for delivery of calbindin-$D_{28k}$ to a cell. These include the use of naked DNA and calbindin-$D_{28k}$ plasmids to directly transfer genetic material into a cell (Wolfe et al., 1990); formulations of trapped liposomes encoding a therapeutic calbindin-$D_{28k}$ genetic element (Ledley et. al., 1987) or in proteoliposomes that contain other viral envelope receptor proteins (Nicolau et al., 1983); and calbindin-encoding DNA, or antisense sequence, coupled to a polysineglycoprotein carrier complex. Hence methods for the delivery of nucleotide sequences to cells are well known in the recombinant arts. Such methods for in vitro delivery, further include, but are not limited to: microinjection, calcium phosphatase, lyposomes, lipofectamine transfection and electroporation.

Accordingly, one particular embodiment of the present invention, a therapeutic calbindin-$D_{28k}$ genetic element such as, a DNA, cDNA, RNA, may be directly injected to the bone marrow, specifically osteoblasts or osteocytes, for the production of calbindin-$D_{28k}$ endogenously. This may be useful for the prevention of glucocorticoid induced cell death in various cell types, in particular osteoblasts and osteocytes, and thereby effective in preventing osteoporosis, but also in neuronal cells such as hippocampal cells, thereby possibly being effective for the prevention of glucocorticoid induced neural degeneration. On the other hand, the genetic element containing a calbindin-$D_{28k}$ DNA, cDNA, RNA or polynucleotide sequences coding for the antisense sequence encoding the protein may also be delivered using other appropriate means, including vectors, as herein described, and well known in the recombinant arts. These may be useful in preventing various forms of cancers such as prostate cancer and the various forms of lymphocytic cancers such as leukemia and lymphoma.

Genetic material, such as the nucleotides of the present invention, may be delivered to cells, in vivo, using various different plasmid based delivery platforms, including but not limited to recombinant ADV (such as that described in U.S. Pat. No. 6,069,134 incorporated by reference herein), AAV (such as those described by U.S. Pat. No. 5,139,941 incorporated by reference herein), MMLV, Herpes Simplex Virus (U.S. Pat. No. 5,288,641, Incorporated by reference herein), cytomegalovirus lentiviral, and overall, retroviral gene delivery systems, well known and practiced with in the art.

Techniques for preparing replication defective, infective viruses are well known in the art, as exemplified by Ghosh-Choudhury & Graham (9187); McGory et al. (1988); and Gluzman et al. (1982), each incorporated by reference herein. These systems typically include a plasmid vector including a promoter sequence (such as CMV early promoter) operably linked to the nucleotide coding the gene of interest (inserted into an appropriate gene insertion site; i.e., an IRES site), as well as a terminating signal (such as a Poly-A tail i.e., BGH), and the appropriate mutations so as to make the delivery vehicle replication defective (e.g., Psi sequence deletions) and safe for therapeutic uses. The construction of the appropriate elements in a vector system containing the nucleotides of the present invention is well within the skills of one versed in the recombinant arts.

A great variety of vector and/or expression systems can be used. Such systems include, among others, chromosomal episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia, viruses, adenoviruses, fowl pox viruses, pseudorabies viruses and retroviruses, and vectors derived from combinations thereof such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate calbindin-$D_{28k}$ therapeutic nucleotide sequence may be inserted into an expression system by any of a variety of well-known and routine techniques, such as, for example, those set forth in Sambrook et al., Molecular Cloning, A Laboratory Manual (supra).

Promoter regions can be selected from any desired gene using CAT (chloramphenicol acetyl transferase) vectors or other vectors with selectable markers. Two appropriate vectors are pKK232-8 and pCM7. Particular named bacterial promoters include laci, lacZ, T3, T7, gpt, lambda PR, PL and trp. Eukaryotic promoters include CMV immediate early, HSV thymidine kinase, early and late SV40, LTRs from retrovirus, and mouse metallothionein-1. Selection of the appropriate vector and promoter is well within the level of ordinary skill in the art. A particularly good promoter for in vivo use would be to use a promoter specific to osteoblasts for instance the osteocalcin, calcium binding protein promoter, which would only allow transcription in osteoblastic cells.

Further still, the therapeutic calbindin-$D_{28k}$ genetic elements such as DNA, cDNA, RNA or polynucleotide sequences coding for the antisense sequence encoding the protein, may be delivered to the cells of the bone marrow, specifically to osteoblasts or osteocytes, for the production or inhibition of calbindin-$D_{28k}$ endogenously, by use of biologically compatible carriers or excipients. This may be useful in inducing or inhibiting programmed cell death. Pharmaceutically acceptable carriers for therapeutic use are well known in the pharmaceutical arts, and are described, for example, in Remington's Pharmaceutical Sciences (A. P. Gennaro, ed.; Mack, 1985). For example, sterile saline or phosphate-buffered saline at physiological pH may be used. Preservatives, stabilizers, dyes, and even flavoring agents may be provided in the pharmaceutical composition. For example, sodium benzoate, sorbic acid, and esters of p-hydroxybenzoic acid may be added as preservatives. Antioxidants and suspending agents may also be used.

The above-described constructs, plasmids and vectors are useful in gene therapy procedures. Successful gene therapy generally requires the integration of a gene capable of correcting the genetic disorder into the host genome, where it would co-exist and replicate with-the host DNA and be expressed at a level to compensate for the defective gene. Ideally, the disease would be cured by one or a few treatments, with no serious side effects. There are several approaches to gene therapy proposed.

As described above, basic transfection methods exist in which DNA containing the gene of interest is introduced into cells non-biologically, for example, by permeabilizing the cell membrane physically or chemically. Liposomes or protein conjugates formed with certain lipids and amphophilic peptides can be used for transfection. (Stewart et al., 1992; Torchilin et al., 1992; Zhu et al., 1993, incorporated herein by reference.) This approach is particularly effective in ex vivo procedures involving osteocytes, which can be temporarily removed from the body and can tolerate the structural manipulation of the treatment.

A basic transduction approach capitalizes on the natural ability of viruses to enter cells, bringing their own genetic material with them. For example, retroviruses have promise as gene delivery vectors due to their ability to integrate their genes into the host genome, transferring a large amount of foreign genetic material, infecting a broad spectrum of species and cell types and of being packaged in special cell-lines (Miller, 1992, incorporated herein by reference).

A third method uses other viruses, such as adenovirus, herpes simplex viruses (HSV), cytomegalovirus (CMV), and adeno-associated virus (AAV), which are engineered to serve as vectors for gene transfer. Although some viruses that can accept foreign genetic material are limited in the number of nucleotides they can accommodate and in the range of cells they infect, these viruses have been demonstrated to successfully effect gene expression. For example, adenovirus gene transfer systems may be used. Such a system is based upon recombinant, engineered adenovirus which is rendered replication-incompetent by deletion of a portion of its genome, such as E1, and yet still retains its competency for infection. Relatively large foreign proteins can be expressed when additional deletions are made in the adenovirus genome. For example, adenoviruses deleted in both E1 and E3 regions are capable of carrying up to 10 Kb of foreign DNA and can be grown to high titers in 293 cells (Stratford-Perricaudet and Perricaudet, 1991a). Surprisingly persistent expression of transgenes following adenoviral infection has also been reported.

Hence, in one particular aspect the invention features a recombinant calbindin-$D_{28k}$ DNA or RNA molecule comprising a vector having an insert that includes part or all of a calbindin-$D_{28k}$ polynucleotide, or its antisense polynucleotide sequence. The invention also features a vector containing a calbindin-$D_{28k}$ polypeptide. Pharmaceutical compositions containing a biologically effective amount of the calbindin-$D_{28k}$ polynucleotide, antisense sequence, protein and/or protein fragments with acceptable carriers are also provided.

Specifically, in a particular embodiment, the invention relates to the administration of vectors for the delivery of a calbindin-$D_{28k}$ therapeutic element to a cell for the treatment of diseases associated with an abnormal increase or decrease in cell death, wherein the vector contains an expression cassette encoding the calbindin-$D_{28k}$ therapeutic. The calbindin-$D_{28k}$ therapeutic can be a CALBINDIN-$D_{28k}$ polynucleotide, a CALBINDIN-$D_{28k}$ polynucleotide antisense sequence, a CALBINDIN-$D_{28k}$ protein or a CALBINDIN-$D_{28k}$ protein fragment. The expression cassette may contain one or more of the following elements: a host cell origin of replication, a suitable promoter operably linked to a heterologous genetic element, an internal ribosome entry site, splice donor site, splice acceptor site, a suitable enhancer, PPT track, heterologous genetic element, a reporter gene, and/or an appropriate termination sequence. One or more of these vectors, containing a calbindin-$D_{28k}$ therapeutic, may be introduced into an appropriate cell by a variety of means, including in vivo, in vitro or ex vivo transduction or transfection using an appropriate expression system.

Delivery/Administration of Calbindin-$D_{28k}$ Therapeutics

The pharmaceutical compositions of the present invention may be formulated and used as tablets, capsules, or elixirs for oral administration; suppositories for rectal or vaginal administration; sterile solutions and suspensions for parenteral administration; creams, lotions, or gels for topical administration; aerosols or insufflations for intratracheobronchial administration; and the like. Preparations of such formulations are well known to those skilled in the pharmaceutical arts. The dosage and method of administration can be tailored to achieve optimal efficacy and will depend on factors that those skilled in the medical arts will recognize.

When administration is to be parenteral, such as intravenous on a daily basis, injectable pharmaceuticals may be prepared in conventional forms, either-as liquid solutions or suspensions solid forms suitable for solution or suspension in liquid prior to injection; or as emulsions. Suitable excipients are, for example, water, saline, dextrose, mannitol, lactose, lecithin, albumin, sodium glutamate, cysteine hydrochloride, or the like. In addition, if desired, the injectable pharmaceutical compositions may contain minor amounts of nontoxic auxiliary substances, such as wetting agents, pH buffering agents, and the like. If desired, absorption enhancing preparations (e.g. liposomes) may be utilized.

Hence, in another preferred embodiment the present invention is directed to a novel pharmaceutical composition that includes a biologically acceptable carrier along with an effective amount of a therapeutic calbindin-$D_{28k}$ genetic element such as a calbindin-$D_{28k}$ DNA, cDNA, RNA or protein for the treatment and/or prevention of diseases associated with an abnormal or increased rate of apoptosis. The pharmaceutical composition includes a calbindin-$D_{28k}$ sequence substantially identical to SEQ ID No. 1 and/or a protein encoded by an amino acid sequence substantially identical to the sequence of SEQ ID No. 2. For the treatment of and/or prevention of diseases associated with an unhealthy decrease in regulated cell death, a pharmaceutical composition that includes an effective amount of a nucleotide sequence coding for the antisense sequence of SEQ. ID. NO:1, may be administered. An example of such diseased state that may be treated by the compositions of the present invention are osteoblastic or osteocytic cancer, as well as hormone independent prostate cancer.

The methods for the treatment of diseases associated with an unhealthy increase of programmed cell death in a subject are also provided. These methods involve administering to the subject a pharmaceutical composition that includes an effective amount of a therapeutic calbindin-$D_{28k}$ genetic element, which may include a calbindin-$D_{28k}$ protein or a nucleotide sequence coding for the calbindin-$D_{28k}$ protein or a nucleotide sequence that codes for the antisense sequence of the nucleotide sequence coding for the calbindin-$D_{28k}$ protein (wherein an increased rate of cell death is sought). These may be delivered by suitable means, as described above, including the use of vectors and or acceptable biological carriers.

For administration, the therapeutic agent will generally be mixed, prior to administration, with a non-toxic, pharmaceutically acceptable carrier substance. Usually, this will be an aqueous solution, such as normal saline or phosphate-buffered saline (PBS), Ringer's solution, lactate-Ringer's solution, or any isotonic physiologically acceptable solution for administration by the chosen means. Preferably, the solution is sterile and pyrogen-free, and is manufactured and packaged under current Good Manufacturing Processes (GMP's), as approved by the FDA. The clinician of ordinary skill is familiar with appropriate ranges for pH, tonicity, and additives or preservatives when formulating pharmaceutical compositions for administration by intravascular injection, intrathecal injection, injection into the bone marrow, direct injection into the osteoblast cell, or by other routes. In addition to additives for adjusting pH or tonicity, the therapeutics agent may be stabilized against aggregation and polymerization with amino acids and non-ionic detergents, polysorbate, and polyethylene glycol.

Optionally, additional stabilizers may include various physiologically acceptable carbohydrates and salts. Also, polyvinylpyrrolidone may be added in addition to the amino acid. Suitable therapeutic immunoglobulin solutions, which are stabilized for storage and administration to humans, are described in U.S. Pat. No. 5,945,098, incorporated fully herein by reference. Other agents, such as human serum albumin (HSA), may be added to the therapeutic composition to stabilize the antibody conjugates. The compositions of the invention may be administered using any medically appropriate procedure, e.g., intravascular (intravenous, intraarterial, intracapillary) administration, inject-ion into the bone marrow, intracavity or direct injection in the osteoblast cell. Intravascular injection may be by intravenous or intraarterial injection.

The effective amount of the therapeutic composition to be given to a particular patient will depend on a variety of factors, several of which will be different from patient to patient. A competent clinician will be able to determine an effective amount of a therapeutic composition to administer to a patient to retard or promote apoptosis in target cells, such as osteoblasts. Dosage of the therapeutic will depend on the type of treatment, route of administration the nature of the therapeutics, sensitivity of the cell to the therapeutics, etc. Utilizing $LD_{50}$ animal data, and other information available for the administration of such compositions a clinician can determine the maximum safe dose for an individual, depending on the route of administration. For instance, an intravenously administered dose may be more than an intrathecally administered dose, given the greater body of fluid into which the therapeutic composition is being administered. Similarly, compositions, which are rapidly cleared from the body, may be administered at higher doses, or in repeated doses, in order to maintain a therapeutic concentration. Utilizing ordinary skill, the competent clinician will be able to optimize the dosage of a particular therapeutic composition in the course of routine clinical trials.

Typically the dosage will be 0.001 to 100 milligrams of therapeutic per Kilogram subject body weight. Doses in the range of 0.01 to 1 mg per kilogram of patient body weight may be utilized for a therapeutic composition that is administered. The therapeutic can be administered to the subject in a series of more than one administration. For therapeutic compositions, regular periodic administration (e.g., every 2-3 days) will sometimes be required, or may be desirable to reduce toxicity. For therapeutic compositions that will be utilized in repeated-dose regimens, moieties that do not provoke HAMA or other immune responses are preferred.

The foregoing is intended to be illustrative of the embodiments of the present invention, and are not intended to limit the invention in any way. Although the invention has been described with respect to specific modifications, the details thereof are not to be construed as limitations, for it will be apparent that various equivalents, changes and modifications may be resorted to without departing from the spirit and scope thereof and it is understood that such equivalent embodiments are to be included herein. All publications and patent applications are herein incorporated by reference to the same extent as if each individual publication or patent application was specifically and individually indicated to be incorporated by reference.

EXAMPLES

The following description sets forth the general procedures involved in practicing the present invention. To the extent that specific materials are mentioned, it is merely for purposes of illustration and is not intended to limit the invention. Unless other-wise specified, general cloning procedures, such as those set forth in Sambrook et al., *Molecular Cloning* supra or Ausubel et al. (eds) *Current Protocols in Molecular Biology*, John Wiley & Sons (2000) are used.

Example 1

A. Materials

Calbindin-$D_{28k}$ was purified from rat kidney, as described previously (Pansini, A. R., and Christakos, S. (1984) J. Biol. Chem. 259, 9735-9741). Purified rat bone osteocalcin was purchased from Biomedical Technologies Inc. (Stoughton, Mass.). Purified bovine calbindin-$D_{28k}$, S100, calmodulin, murine gelsolin, and antibody to [−]actin were purchased from Sigma. The caspase-3 activity assay kit, recombinant and purified human caspase-3, and the cell-permeable caspase-3 inhibitor Asp-Glu-Val-Asp-aldehyde (DEVD-CHO) (SEQ ID NO:4) were obtained from Biomol Research Laboratories, Inc. (Plymouth Meeting, Pa.). The glucocorticoid dexamethasone can be obtained from several commercial sources. SUPERFECT®, LIPOFECTIN®, and ECL™™ reagents were purchased from QIAGEN® (Santa Clarita, Calif.), Life Technologies, Inc., and NEN Life Science Products, respectively. The enhanced green fluorescent protein (CLONTECH™) Laboratories, Palo Alto, Calif.) containing the SV40 large T antigen nuclear localization sequence (Kalderon, D., Roberts, B. L., Richardson, W. D., and Smith, A. E. (1984) Cell 39, 499-509) attached to the carboxyl terminus was provided by Dr. Charles O'Brien (University of Arkansas for Medical Sciences, Little Rock, Ark.).

B. Cell Culture Conditions

Murine osteocytic MLO-Y4 cells (provided by Dr. Lynda Bonewald, University of Texas Health Center at San Antonio, Tex.), and primary bone cells (isolated from neonatal murine calvaria) were cultured as indicated previously (Kato, Y., Windle, J. J., Koop, B. A., Mundy, G. R., and Bonewald, L. F. (1997) *J. Bone Miner Res.* 12, 2014-2023) (Bellido, T., Borba, V. Z. C., Roberson, P. K., and Manolagas, S. C. (1997) *Endocrinology* 138, 3666-3676). All culture media contained 100 units/ml penicillin and 100 μg/ml streptomycin. Cultures were kept in a humidified atmosphere of 5% $CO_2$ in air at 37° C.

C. Transient and Stable Transfections of Calbindin-$D_{28k}$

Transient transfections of MLO-Y4 cells were carried out in 12-well culture plates using SUPERFECT®. Cells (0.1×$10^6$/well) were transfected in triplicate, using lipofectamine, with 2 μg of the expression vectors pBSR (a gift of Dr. Michael Olszowy, Washington University School of Medicine, St. Louis, Mo.) or pREP4 (Invitrogen, Carlsbad, Calif.), alone or containing the cDNA for calbindin-$D_{28k}$. The calbindin-$D_{28k}$ expression plasmids were prepared using the full-length calbindin-$D_{28k}$ cDNA isolated by reverse transcriptase-polymerase chain reaction from rat renal distal tubular mRNA. For the establishment of MLO-Y4 cells expressing different levels of calbindin-$D_{28k}$, parent MLO-Y4 cells were transfected with pREP4 or pREP4-calblndin-$D_{28k}$ as described in Guo, Q., Christakos, S., Robinson, N., and Mattson, M. P. (1998) *Proc. Natl. Acad. Sci. U S. A.* 95, 3227-3232. MLO-Y4 cells were then cultured in αMEM (phenol red free) supplemented with 5% FBS, 5% bovine calf serum, 100 U/ml penicillin and 100 μg/ml streptomycin. Cells were plated at $1\times10^4$ to $2\times10^4$ cells/cm$^2$ on collagen I-coated plates. After 6, 12 and 24 h, apoptosis was induced by addition of $10^{-6}$ M dexamethasone and quantified as indicated below or cell lysates collected for the analysis of calbindin-$D_{28k}$ by Western blotting and radioimmunoassay (cite 65 of grant).

D. Apoptosis

Cell viability was monitored by trypan blue exclusion. Nonadherent cells were combined with adherent cells released from the culture dish using trypsin-EDTA, resuspended in medium containing serum and collected by centrifugation. 0.04% trypan blue was added and the 150 cells per condition are counted). DNA fragmentation was measured by the TUNEL (transferase biotin-dUTP nick endlabeling). We have previously demonstrated that the percentage of cells exhibiting trypan blue staining correlates with the percentage of terminal deoxynucleotidyl transferase-mediated nick end labeling-labeled cells, indicating that apoptotic osteoblasts could be reliably quantified by either method (Jilka, R. L., Weinstein, R. S., Bellido, T., Parfitt, A. M., and Manolagas, S. C. (1998) *J. Bone Miner Res.* 13, 793-802; Jilka, R. L., Weinstein, R. S., Bellido, T., Roberson, P. K., Parfitt, A. M., and Manolagas, S. C. (1999) *J. Clin. Invest.* 104, 439-446; Plotkin, L. I., Weinstein, R. S., Parfitt, A. M., Roberson, P. K., Manolagas, S. C., and Bellido, T. (1999) *J. Clin. Invest.* 104, 1363-1374; and Bellido, T., O'Brien, C. A., Roberson, P. K., and Manolagas, S. C. (1998) *J. Biol. Chem.* 273, 21137-21144).

After 6, 12 and 24 h in the presence or absence of dexamethasone cells were fixed, permeabilized (0.1% Triton×100 in 0.1% citrate), washed and labeled using terminal deoxynucleotidyl transferase (TdT) which catalyzes the addition of fluorescein dUTP at free 3'OH groups in single and double stranded DNA. Cells were then washed and analyzed by fluorescence microscopy (a negative control included all steps without the addition of terminal transferase (In situ cell death detection kit, Boehringer Mannheim). Cells were also examined microscopically to assess morphological changes in the presence of dexamethasone and in the presence or absence of calbindin.

F. Western Blot Analysis and Radioimmunoassay

Cell lysates, protein electrophoresis and Western blot analysis were performed as described previously (Bellido, T., Borba, V. Z. C., Roberson, P. K., and Manolagas, S. C. (1997) *Endocrinology* 138, 3666-3676). Membranes were incubated overnight at 4° C. with an antibody to either calbindin-$D_{28k}$ (Sonnenberg J., Pansini, A. R., and Christakos, S. (1984) *Endocrinology* 115, 640-648) or -actin, followed by incubation for 1 h with the corresponding secondary antibody conjugated with horseradish peroxidase. Blots were developed by ECL™. Quantification of the intensity of the bands in the autoradiograms was performed by laser densitometry. Calbindin-$D_{28k}$ protein levels were determined by radioimmunoassay using antiserum against rat renal calbindin-$D_{28k}$ and purified rat renal calbindin-$D_{28k}$ as standard, as described previously (Sonnenberg, J., Pansini, A. R., and Christakos, S. (1984) *Endocrinology* 115, 640-648).

F. In Vitro Digestion with Caspase-3

Purified gelsolin (3 μg) or calbindin-$D_{28k}$ (3 μg) and caspase-3 (50 ng) were incubated at 37° C. for 10 min in 6 mM Tris-HCI (pH 7.5), 1.2 mM $CaCl_2$, 1.5 mM dithothreitol, 1.5 mM $MgCl_2$, and 1 mM KCI. Samples were analyzed by SDS-PAGE followed by staining with Coomassie Blue.

G. Caspase-3 Activity

Since dexanethasone induced apoptosis in MLO-Y4 cells and in primary osteoblasts has been shown to be accompanied by activation of caspase 3 (cite 47 of grant) and since we predicted that Calbindin-$D_{28k}$ inhibits caspase 3 (cite 29 of grant), we examined MLO-Y4 cells for an increase in caspase 3 in response to dexamethasone and used calbindin-$D_{28k}$ transfected MLO-Y4 cells to determine whether calbindin-$D_{28k}$ blocks dexamethasone induced caspase 3 activity in these cells. Caspase 3 activity was measured by the degradation of the colorimetric caspase 3 substrate DEVD-paranitroanilide (DEVD-pNA) that contains the sequence of the caspase 3 cleavage site in poly(ADP-ribose) polymerase (Schiegel, J., Peters, I., Orrenihus, S., Miller, D. K., Thornberry, N. A., Yamin, T. T., and Nicholson, D. W. (1996) *J. Biol. Chem.* 271, 1841-1844) (cite 110 of grant). Cell pellets obtained from MLO-Y-4 cells transfected with calbindin-$D_{28k}$ or vector and treated with dexamethasone was resuspended in lysis buffer (50 mM Hepes pH 7.4, 0.1% CHAPS, 1 mM DDT, 0.1 mM EDTA, 0.1% Triton×100). After centrifugation (20,000×g 10 min) 30-100 μg cell lysate was added to the assay buffer (50 mM Hepes. 100 mM NaCl, 0.1% CHAPS, 10% v/v glycerol, 1 mM EDTA and 10 mM DDT) containing 200 μM DEVD-PNA (total volume=100 ul). Incubation was at 37° C. and plate absorbency was read at 405 nm every 10 min up to 120 min in a microtiter plate reader. As a positive control purified caspase 3 (30 U) was incubated with DEVD-pNA. As an additional control the specific inhibitor of caspase 3 (DEVD-CHO) can be added to cell lysates (0.1 μM) to control for any non-specific hydrolysis of DEVD-pNA. The caspase 3 assay (BIOMOL QuantiZyme Assay System) may be used for these purposes.

H. Results of Analysis

Figure 1:
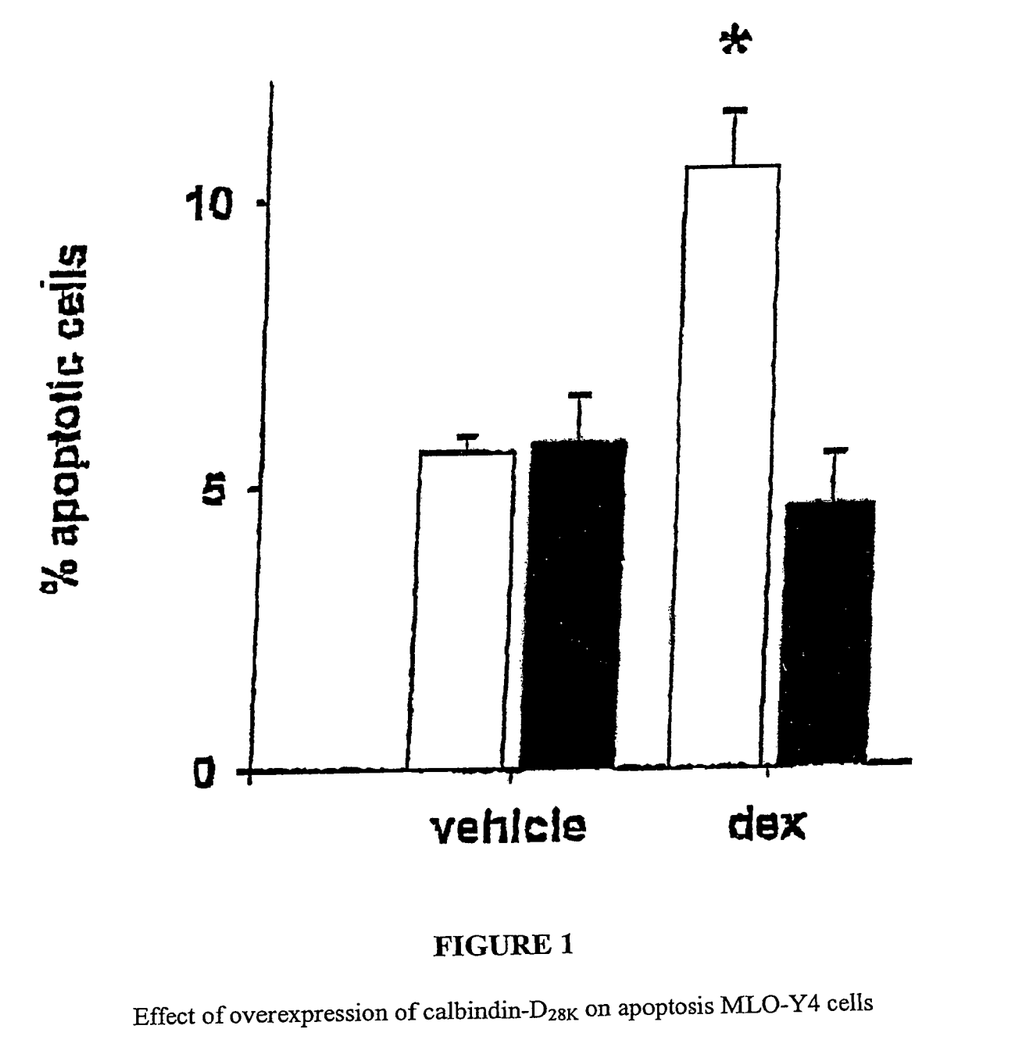
FIG. 1 shows calbindin-$D_{28K}$ protection against dexamethasone induced cell death of MLOY4 osteocytic cells.

Data were analyzed by one-way analysis of variance, and the Student-Keuls-Newman method was used to estimate the level of significance of differences between means. The effect of dexamethasone treatment and Calbindin-$D_{28k}$ overexpression on the proportion of apoptotic cells in the experiment of FIG. 1 was analyzed using exact procedures for logistic regression (Otulsky, H. (1995) *Intuitive Biostatistics*, Oxford University Press, New York) (LogXact software; CYTEL Software Corp.; Cambridge, Mass.). Following this, individual pair-wise comparisons of experimental groups were conducted using exact tests, adjusting the p values with a Bonferroni correction. All p values (unadjusted for logistic regression; Bonferroni-adjusted for individual group comparisons) were compared with a value of 0.05 to determine significance. Findings shown in FIG. 1 show the protection by calbindin-$D_{28k}$ against glucocorticoid induced apoptosis.

Example 2

A. Further Analysis

In addition to MLO-Y4 cells, it will also be possible to determine the effect of dexamethasone in the presence or absence of calbindin-$D_{28k}$ on apoptotic cell death and on caspase 3 activity (with the methodology outlined above) using primary osteoblastic cells from calbindin-$D_{28k}$ KO and WT mice. Murine osteoblasts will be isolated from pups 30-72 h old from our colony of WT (C57BL6) or calbindin-$D_{28k}$ KO mice (cite 22 of grant, cite 111 of grant) by controlled digestion with collagenase (cite 112 of grant). Briefly calvariae, trimmed of fibrous tissue and divided in 2 are transferred to 15 ml conical sterile tubes, washed with PBS (5 ml) 3× at 37° C. (10 min/wash) in an oscillating $H_2O$ bath. Calvariae are then subjected to a series of collagenase digestions (200 μg/Ml PBS collagenase CLS2 from Worthington) in an oscillating 37° C. $H_2O$ bath (calvariae from 5-10 mice/ approx. 5 ml collagenase buffer/10 mm. followed by low speed centrifugation and resuspension of the pellet and repeat digestion). The first 2 digests are discarded and digests from 3, 4 and 5 are neutralized with MEM, pooled, filtered through sterile mesh. The filtrate is centrifuged for 6 min. at 1500 rpm, the supernatant removed and the cells resuspended in 3-5 ml MEM containing 100% FCS. After isolation cells are cultured in 10% FB5 at $1\times10^4$ to $2\times10^4$ cells/cm2. In preliminary studies using primary osteoblasts K. Gengaro found that after 16 h dex. treatment ($10^{-6}M$) the % of dead cells (assayed by trypan blue uptake) was 23.2±3 in the absence of calbindin-$D_{28k}$ and 12.9±2.4 in the presence of calbindin-$D_{28k}$ ($p<0.05$). This experiment will be important in determining that there is an increase in capase 3 activity after glucocorticoid treatment and establishing that calbindin-$D_{28k}$ inhibits that increase in bone cells. The ability of calbindin-$D_{28k}$ to protect against induction of other caspases such as caspase 6, 7, 9 and 10 will also be examined in accordance with the experiments set forth above.

---

What is claimed is:

1. A vector suitable for use in a human cell comprising a polynucleotide having the sequence set forth in SEQ ID NO:1, wherein said polynucleotide is operably linked to a promoter specific to osteoblasts and said polynucleotide encodes a calbindin-$D_{28k}$ polypeptide which inhibits apoptosis.

2. A pharmaceutical composition suitable for use in a human cell comprising a biologically effective amount of a CALBINDIN-$D_{28k}$ polynucleotide encoding a calbindin-$D_{28k}$ polypeptide having the amino acid sequence set forth in SEQ ID NO:2, and an acceptable carrier, wherein the CALBINDIN-$D_{28k}$ polynucleotide is operably linked to a promoter specific to osteoblasts.

3. The composition of claim 2, wherein the CALBINDIN-$D_{28k}$ polynucleotide has the sequence set forth in SEQ ID NO:1.

4. A vector for expression of a calbindin-$D_{28k}$ protein in a human cell, wherein the vector comprises an expression cassette including a promoter specific to osteoblasts operably linked to a polynucleotide encoding a calbindin-$D_{28k}$ protein having the amino acid sequence set forth in SEQ ID NO:2, wherein the protein inhibits apoptosis.

5. The vector of claim 4, wherein the expression cassette comprises one or more elements selected from the group consisting of a host cell origin of replication, suitable promoter operably linked to a heterologous genetic element, internal ribosome entry site, splice donor site, splice acceptor site, suitable enhancer, heterologous genetic element, a reporter gene, and an appropriate termination sequence.

6. The vector of claim 4, wherein the vector is selected from the group consisting of: retrovirus, lentivirus, adenovirus, herpes simplex viruses (HSV), cytomegalovirus (CMV), and adeno-associated virus (AAV).

* * * * *